United States Patent
Ralfs

(10) Patent No.: US 8,201,558 B2
(45) Date of Patent: Jun. 19, 2012

(54) METHOD FOR OPERATING AN ANESTHESIA OR VENTILATION APPARATUS HAVING A TRIGGER FUNCTION AND DEVICE THEREFOR

(75) Inventor: Frank Ralfs, Lübeck (DE)

(73) Assignee: Draeger Medical GmbH, Luebeck (DE)

( * ) Notice: Subject to any disclaimer, the term of this patent is extended or adjusted under 35 U.S.C. 154(b) by 892 days.

(21) Appl. No.: 12/216,387

(22) Filed: Jul. 3, 2008

(65) Prior Publication Data

US 2009/0007916 A1    Jan. 8, 2009

(30) Foreign Application Priority Data

Jul. 4, 2007 (DE) .......................... 10 2007 031 017

(51) Int. Cl.
*A61M 16/00* (2006.01)
*A62B 7/00* (2006.01)
*F16K 31/02* (2006.01)

(52) U.S. Cl. ......... 128/204.23; 128/204.18; 128/204.21; 128/203.14

(58) Field of Classification Search ............. 128/203.12, 128/203.14, 204.18, 204.21, 204.23
See application file for complete search history.

(56) References Cited

U.S. PATENT DOCUMENTS

| | | | | |
|---|---|---|---|---|
| 4,387,722 A * | 6/1983 | Kearns | .......................... | 600/529 |
| 5,188,098 A * | 2/1993 | Hoffman et al. | ......... | 128/204.23 |
| 6,431,171 B1 | 8/2002 | Burton | | |
| 7,438,686 B2 | 10/2008 | Cho et al. | | |
| 2002/0056454 A1 * | 5/2002 | Samzelius | ................ | 128/204.23 |
| 2005/0087190 A1 * | 4/2005 | Jafari et al. | .............. | 128/204.21 |

FOREIGN PATENT DOCUMENTS

WO    WO 2005/096924    10/2005

OTHER PUBLICATIONS

Imanaka et al. Autotriggering caused by cardiogenic oscillation during flow-triggered mechanical ventilation. Crit. Care Med. 2000; 28(2); 402-407.*
Lichtwarck-Aschoff et al. Decreasing size of cardiogenic oscillations reflects decreasing compliance of the respiratory system during long-term ventilation. J. Appl. Physiol. 2004; 96; 879-884.*
Cole. Cardiogenic oscillations and apparent ventilation in suspected brain death. Resuscitation 2003; 56; 335.*
Wijdicks et al. Ventilator self-cycling may falsely suggest patient effort during brain death determination. Neurology 2005; 65; 744.*
Hill et al. Flow triggering, pressure triggering and autotriggering during mechanical ventilation. Crit. Care Med. 2000; 28(2) 579-581.*
Coxon et al. Autotriggering of pressure support ventilation during general anaesthesia. Anaesthesia 2006; 61; 64-75.*
Willatts et al. Brainstem death and ventilator trigger settings. Anaestesia 2000; 55; 676-684.*

* cited by examiner

*Primary Examiner* — Loan Thanh
*Assistant Examiner* — Kathryn D Sheikh
(74) *Attorney, Agent, or Firm* — Walter Ottesen

(57) ABSTRACT

A method for operating an anesthesia/ventilation apparatus (11) avoids cardiogenic triggering of a triggered ventilation stroke. An apparatus (11) for carrying out the method of the invention is also disclosed.

11 Claims, 4 Drawing Sheets

METHOD FOR OPERATING AN ANESTHESIA OR VENTILATION APPARATUS HAVING A TRIGGER FUNCTION AND DEVICE THEREFOR

CROSS REFERENCE TO RELATED APPLICATION

This application claims priority of German patent application no. 10 2007 031 017.1, filed Jul. 4, 2007, the entire content of which is incorporated herein by reference.

BACKGROUND OF THE INVENTION

From the state of the art, ventilation apparatus as well as anesthesia apparatus (referred to hereinafter as ventilation apparatus) having units for synchronizing the mechanical ventilation with spontaneous breathing efforts of the patient are known. The more sensitive the corresponding unit for triggering or executing a mechanical ventilation is adjusted, the earlier or more rapidly does the ventilation apparatus react to an inhalation effort of the patient and that much less is the required respiratory activity of the patient.

A sensitively set trigger threshold, however, has the inherent danger of a so-called self-triggering of the ventilation apparatus. Here, mechanical ventilation strokes can be triggered by leakages in the hose system, by oscillating condensate in the ventilating hoses or by oscillations caused by cardiac activity and transmitted to the lung. Such self-triggerings can lead to an overventilation which, inter alia, can cause a respiratory alkalosis, a reduced respiratory drive as well as an extended need for ventilation.

Ventilation apparatus of the state of the art often have a unit for adapting the trigger threshold to leakages in order to avoid a self-triggering caused thereby. In the case of a self-triggering because of cardiogenic oscillations as described above, up to now there is only the possibility to manually raise the trigger threshold so far that the cardiogenically caused oscillations trigger no further ventilation strokes. A disadvantage associated herewith is the time-dependent delay of the start of the triggering, a greater respiratory effort for the patient and a poorer synchronization with the known side effects associated herewith during the actual respiratory efforts of the patient.

SUMMARY OF THE INVENTION

It is an object of the invention to provide a method for operating an anesthesia or ventilation apparatus with trigger functions by means of which at least some of the above-mentioned disadvantages are avoided or can be reduced. It is also an object of the invention to provide an apparatus for carrying out the method of the invention.

The method of the invention is for operating an anesthesia and/or ventilation apparatus which includes a triggering unit. The method includes the steps of: determining whether a predetermined relationship is present between a patient cardiac cycle and a triggering of a triggered ventilation stroke based on patient flow data and on data of the patient cardiac cycle; and, in response to a presence of the predetermined relationship, increasing a triggering threshold for triggered ventilation strokes during only one segment of the patient flow cycle so as to cause the predetermined relationship to no longer be present.

A method for operating an anesthesia or ventilation apparatus is suggested for avoiding or reducing cardiogenic triggering of a triggered ventilation stroke. The method of the invention includes the step of determining whether a predetermined relationship is present between the patient cardiac cycle and the triggering of a triggered ventilation stroke based on patient flow data as well as on data of the patient cardiac cycle.

The patient flow data can be data which can be derived from an inhalation and/or exhalation activity. These data can be measured as volume flows, volumes without time reference or any other suitable manner. The measurements can be made on the patient as well as on the apparatus.

The data of the patient cardiac cycle can, for example, be present as electrocardiograph (ECG) recordings. These data can either be obtained during the execution of the method of the invention or these data can be known from a measurement made in advance of the application of the method of the invention. The data can also be values which were obtained collectively and not from an individual patient.

The method of the invention further includes the step of increasing the triggering threshold when the predetermined relationship between patient cardiac cycle and the triggering of a triggered ventilating stroke (or several ventilating strokes) is present. In this way, satisfying the adequate triggering conditions or reaching or exceeding the triggering threshold for triggered ventilation strokes because of the patient cardiac cycle or because of the occurrence of sections or phases thereof are avoided or at least reduced in their frequency.

A triggered ventilating stroke is triggered when reaching or exceeding a flow trigger threshold or triggering threshold. An increase of the triggering threshold is, according to the invention, an increase of the triggering threshold in the sense of a reduction of the sensitivity for the triggering of a triggered respiratory stroke.

The increase of the triggering threshold can take place automatically, that is, at the apparatus end and without human participation. The increase can also be manually triggered by the person attending the patient. Furthermore, the triggering can, for example, take place in a manner determined in advance by the attendant. This can be prepared in such a manner that an increase by the attendant leads inexorably to an increase which corresponds to a predetermined increase pattern or increase course. In addition, the raising of the triggering threshold by the attendant can take place in a manner suggested by the apparatus taking into account the extent of the oscillations transmitted to the lung.

The increase of the triggering threshold takes place in accordance with the invention during only one section of the patient cardiac cycle in such a manner that the predetermined relationship between the patient cardiac cycle and the triggering of a triggered ventilation stroke is no longer present. A self-triggering of cardiogenic origin is thereby advantageously avoided or reduced with respect to its frequency of occurrence.

As a further advantage of this procedure compared to that of the state of the art, it is noted that the triggering threshold is not increased during the total ventilation duration or anesthesia duration and preferably is not increased over the total duration of one patient cardiac cycle because this would lead to a general reduction of the sensitivity of the method. The adequate trigger conditions or the triggering threshold can only be raised or sharpened during such phases of the patient cardiac cycle wherein a cardiogenic triggering of a self-triggering is to be expected with great probability. In all remaining phases or time segments of the patient cardiac cycle, the originally set sensitivity for the detection of spontaneous respiratory activity of the patient is maintained. Such a phase of increased triggering probability of cardiogenic origin (cardiogenic self-triggering) of the patient cardiac cycle can be the QRS-complex (so-called ventricular complex) in the ECG. However, it can be any other segment or complex which is assignable to cardiac activity which leads to a self-triggering of a mechanical ventilation stroke, that is, a triggering not caused by a respiratory activity of the patient.

Different than in the state of the art, it is advantageously possible, on the one hand, to suppress an occurrence of a cardiogenic self-triggering or to reduce its frequency of occurrence while, on the other hand, to simultaneously maintain the greatest possible sensitivity for the detection of spontaneous respiratory activity of the patient.

Under the term "patient", every living organism (human or animal) is understood which is ventilated by means of an anesthesia and/or ventilation apparatus.

In a preferred embodiment of the invention, the triggering threshold is increased in a segment of the patient cardiac cycle which begins 30 to 60 milliseconds after completing the QRS-complex. Several publications describe that typically within this time interval after the QRS-complex (that is, in the phase of the rapid ventricular contraction) flow trigger thresholds are exceeded in the case of a cardiogenic self-triggering. Correspondingly, a cardiogenic self-triggering is especially effectively countered by an increase of the trigger threshold in this time interval.

In a further embodiment, the predetermined relationship between the occurrence of the phase and the satisfaction of the adequate trigger movement is fixed in data, which are picked up by means of electrocardiography, in such a manner that cardiogenic self-triggering is present when the start of at least 80% of the triggered ventilation strokes of a predetermined time span (which can, for example, be five minutes) lies 30 to 60 milliseconds after completion of a QRS-complex and/or when the cardiac frequency and the respiratory frequency deviate not more than 20% from each other. In this case, the probability is high that cardiogenic self-triggering is present and that the patient profits from an increase of the flow trigger threshold or from a tightening of the adequate trigger condition.

In a further preferred embodiment, the method of the invention includes the step of increasing the triggering threshold in such a manner that the start of at most 60% of the triggered ventilation strokes lies at 30 to 60 milliseconds after completion of the QRS-complex.

Maintaining this trigger condition advantageously makes possible a high residual sensitivity to a spontaneous respiratory activity of the patient while simultaneously avoiding the plurality of cardiogenic self-triggerings of the system.

The tightening of the adequate trigger movement can be limited in time up to completion of the T-wave in the electrocardiogram or up to the return of the patient flow to a value of zero. In this way, an as early as possible renewed responsiveness of the system for a triggering, that is, for the triggering of a mechanical ventilation stroke based on spontaneous respiratory activity of the patient is advantageously ensured at least at a time point within the cardiac cycle of the patient at which a cardiogenic self-triggering can be expected with lower probability because of the only comparatively slight electrophysiological changes on the heart.

In a preferred embodiment, the triggering threshold is increased in steps between 0.5 liters per minute up to 8 liters per minute. This permits a suitable "groping" of the system to an optimal flow trigger threshold which is matched to an increased extent to the individual conditions of the patient. On the one hand, a cardiogenic self-triggering is advantageously effectively prevented while, on the other hand, the sensitivity of the system to spontaneous respiratory activity of the patient is maintained for triggering the triggered ventilation stroke.

In a further preferred embodiment, the triggering threshold is raised by a specific amount which is determined during a time span of non-occurring respiratory efforts (triggered, for example, by temporary hyperventilation, short-term sedation or suitable selection of a time window). For this purpose, a maximum in the patient flow/respiratory flow curve is again determined starting 30 to 60 ms after the QRS-complex up to the completion of the T-wave in the ECG or until the return of the patient flow to a value of zero. Several such maxima averaged over a time span of, for example, one minute, result in the amount by which the flow trigger threshold is raised.

The anesthesia and/or ventilation apparatus of the invention includes: a triggering unit for triggering a triggered ventilation stroke when reaching a triggering threshold; a determination unit for determining whether a predetermined relationship is present between a patient cardiac cycle and the triggering of triggered ventilation strokes based on patient flow data and on data of the patient cardiac cycle; and, an adjusting unit for increasing the triggering threshold when the relationship is present during only one segment of the patient cardiac cycle.

The advantages discussed above with respect to the method of the invention apply also to the above-described apparatus in totality.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
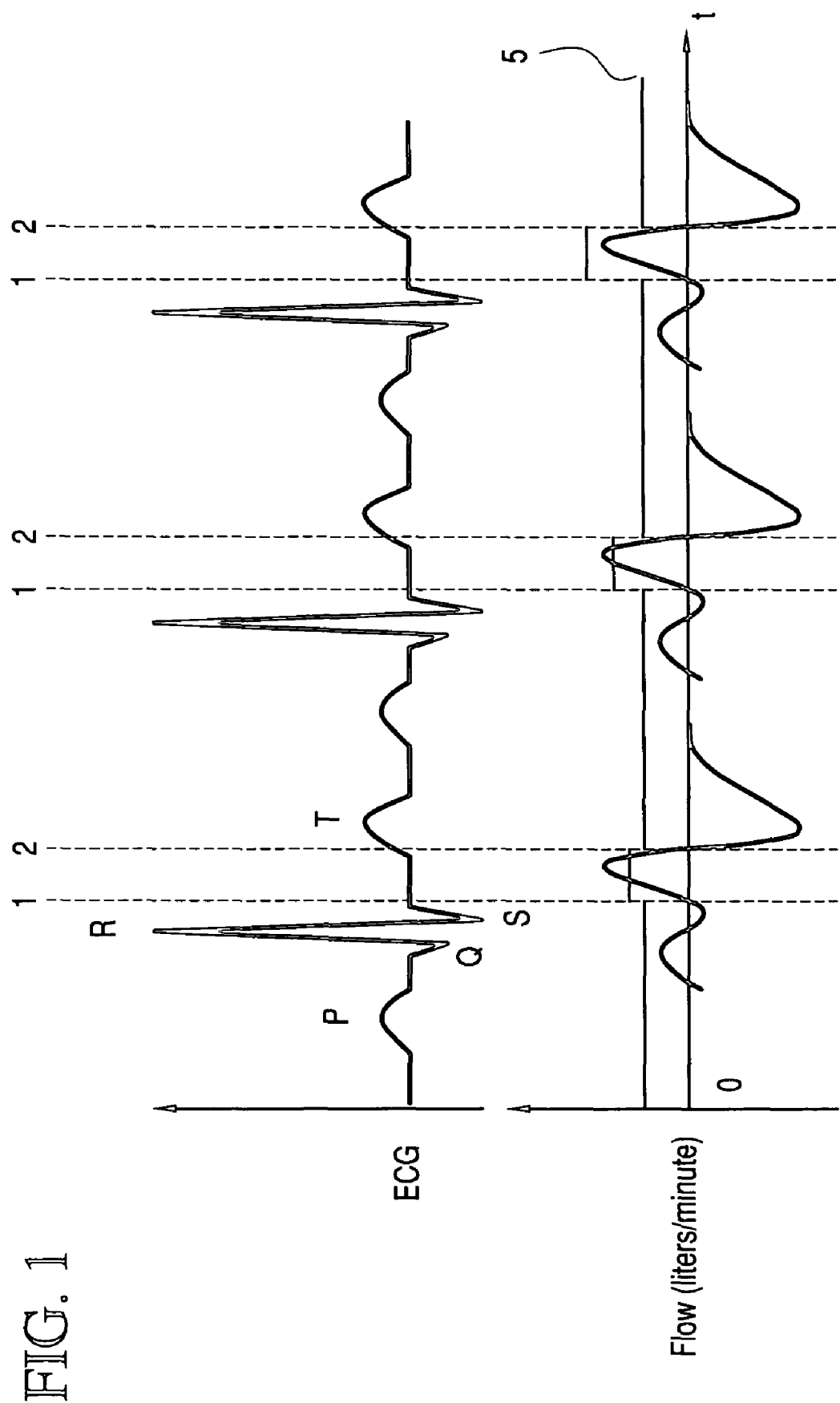
FIG. 1 is a simplified schematic showing the ECG trace of a patient and the corresponding course of flow.

In the upper portion of FIG. 1, a schematically simplified ECG trace of a ventilated patient is shown. In the ECG trace shown, three phases are illustrated and each of these phases contains the numerals 1 and 2. In each phase, the time point 1 identifies the time-dependent completion of the QRS-complex and time point 2 corresponds to the occurrence of the T-wave. The flow curve of the same patient is shown in the lower portion of FIG. 1 and moves about a zero line with this flow curve being synchronized to the ECG trace. A region above the zero line corresponds to the gas take up of the patient, that is, the inhalation (mechanical or spontaneous) and a region below the zero line corresponds to the gas output or the exhalation by the patient. Reference numeral 5 identifies a flow trigger threshold or trigger threshold which is temporarily set higher to avoid cardiac self-triggering each time in a region between QRS-complex and T-wave as likewise shown in FIG. 1 in order not to permit cardiogenic oscillation of the flow curve to be the cause of a self-triggering (not shown here).

FIG. 1 shows that an adaptive increase of the flow-trigger threshold can be provided in accordance with the invention. One recognizes that the flow-trigger threshold, in each case, increases in the region of the three cardiac rhythm phases identified by reference numerals 1 and 2 as a function of time. This increase should take place so long until the above-mentioned condition is just no longer satisfied. The check as to whether a further increase of the flow-trigger threshold is necessary can take place, for example, in accordance with the above-mentioned criteria. These criteria are not shown in FIG. 1 for the sake of a simplified illustration.

Should it not be possible to raise the flow-trigger threshold in such a manner that a cardiogenic self-triggering is prevented to an adequate extent or is reduced, then in each embodiment of the invention, it can be provided that a corresponding alarm is outputted to advise the attending physician.

Figure 2A:
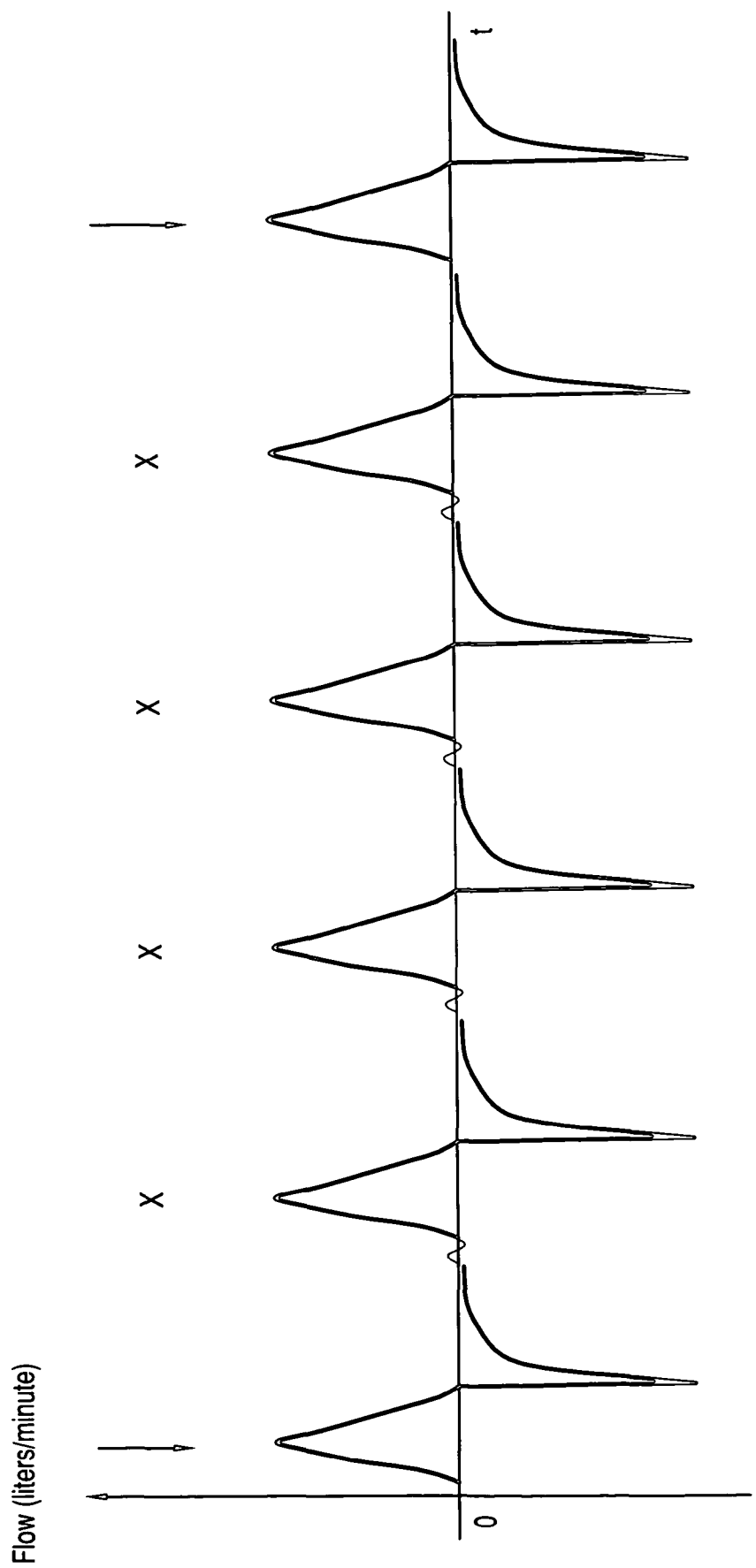
FIG. 2a shows a flow curve of a patient without spontaneous respiratory activity with cardiogenic self-triggering.

FIG. 2*a* shows a flowchart of a patient without spontaneous respiratory activity with a comparatively sensitively adjusted flow-trigger threshold (not shown). Four mechanical ventilation strokes, which are triggered in each case by cardiogenic oscillation, are shown between the ventilation strokes marked in each case by a perpendicular arrow. The disadvantageous effects of these self-triggering ventilation strokes were described above.

Figure 2B:
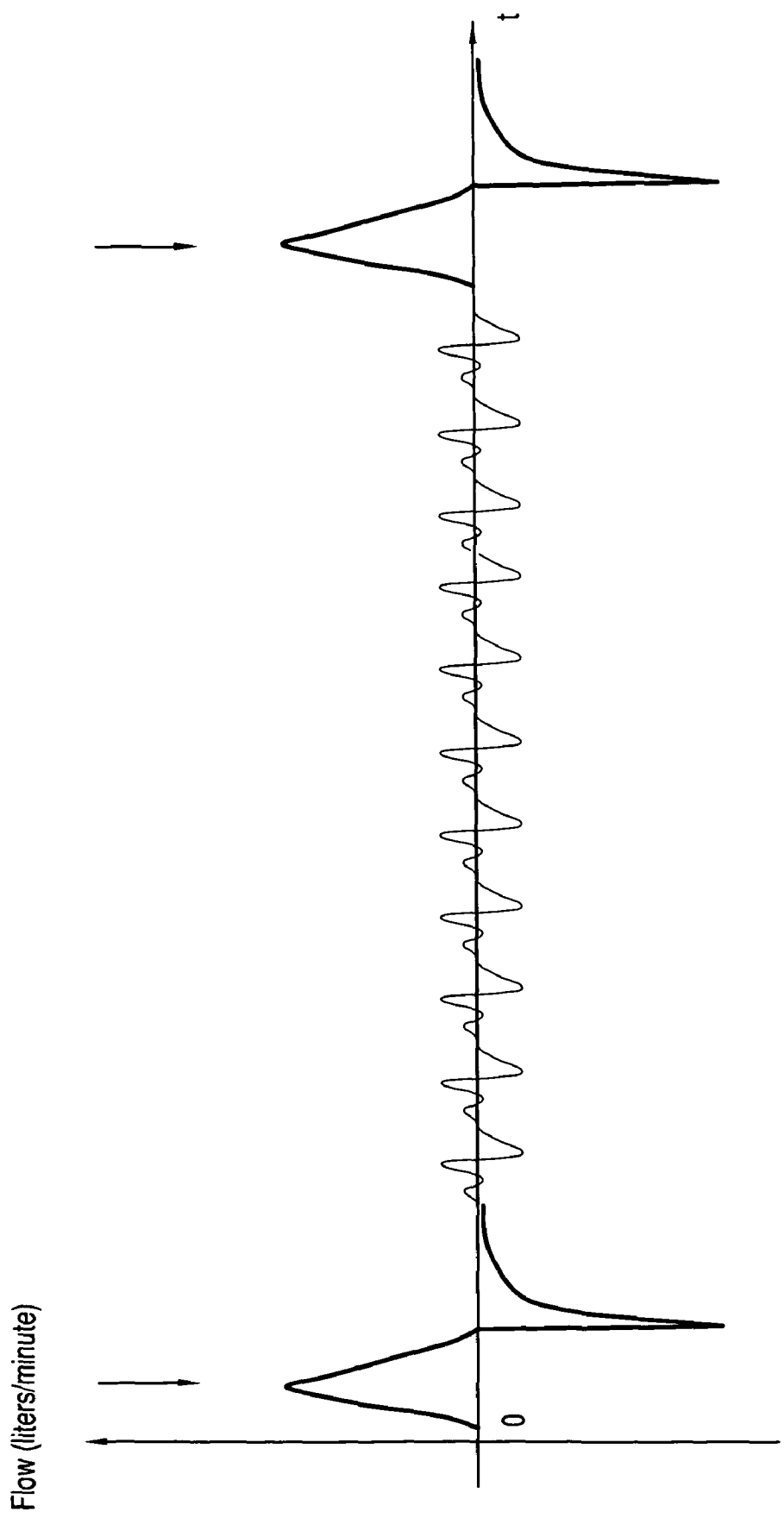
FIG. 2b is a flow curve of a patient without spontaneous respiratory activity with an adapted flow trigger threshold without cardiogenic self-triggering; and, FIG. 3 shows, by way of example, a schematic of an embodiment of the anesthesia or ventilating apparatus according to the invention.

FIG. 2*b* shows the flow curve of the same patient without spontaneous respiratory activity with temporarily adapted flow-trigger threshold. FIG. 2*b* shows that, except for the therapeutically intended breathing strokes (which are marked again by perpendicular arrows) no additional cardiogenic self-triggering ventilation strokes take place which is different than in FIG. 2*a*. The patient performs a significantly lower respiratory activity in the case of spontaneous breathing and the occurrence of a respiratory alkalosis and the reduction of the breathing drive connected therewith are advantageously prevented or at least minimized. The extended need for ventilation is possibly affected hereby.

Figure 3:
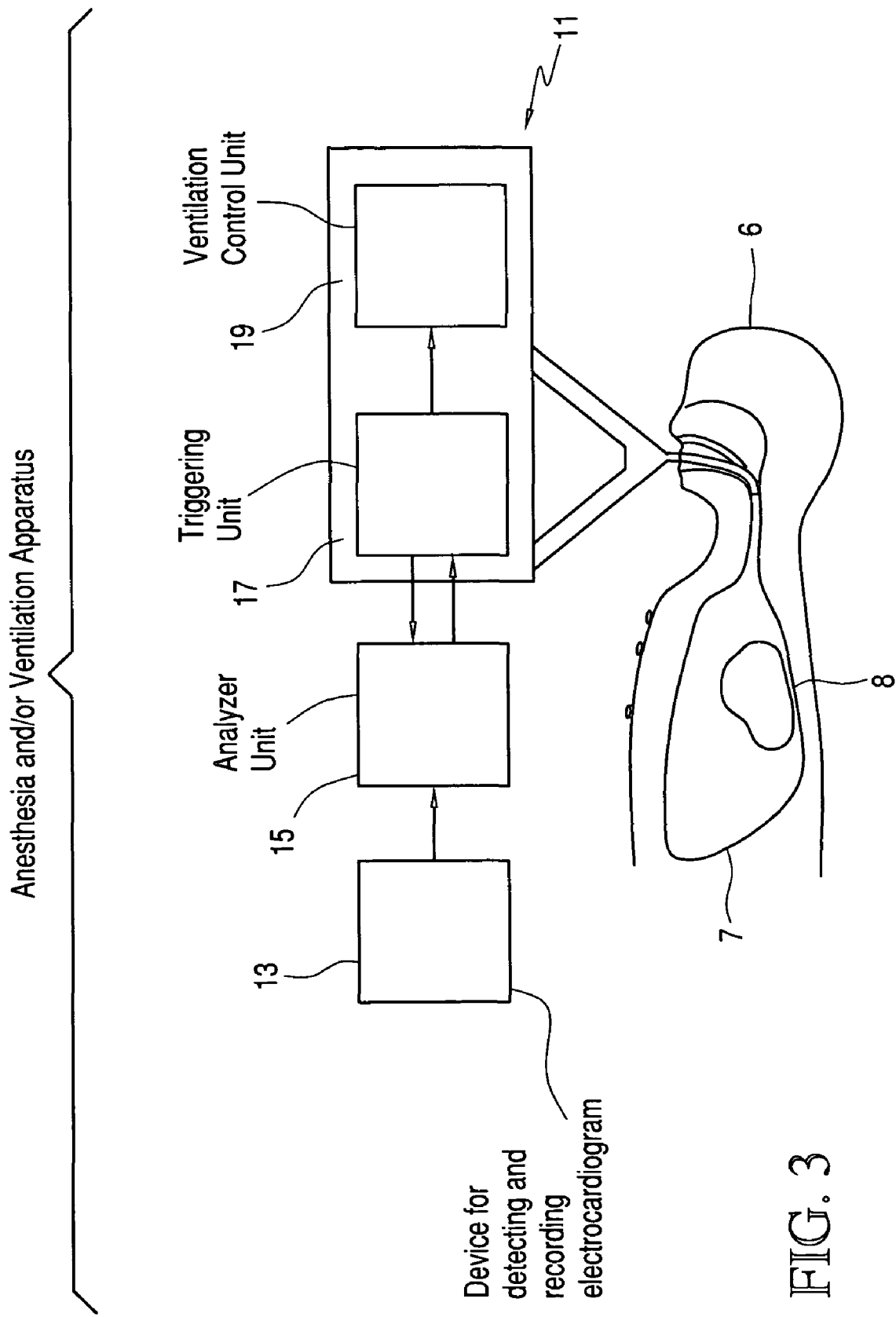

FIG. 3 shows a patient 6 having lungs 7 and a heart 8 which is ventilated with a schematically simplified embodiment of the anesthesia or ventilation apparatus 11 of the invention shown by way of example. The apparatus 11 includes a unit 13 for detecting and recording the activity of the heart 8 as well as of the patient cardiac cycle. This unit 13 can be configured as an ECG measuring device.

The patient cardiac cycle is analyzed by means of an analyzer unit 15 and individual phases of cardiac activity are determined by means of this unit 15.

For measuring the patient flow and for detecting a trigger signal, the ventilation apparatus 11 includes a triggering unit 17. For this purpose, also separate units can be provided. The trigger signal is transmitted to a ventilation control unit 19. The ventilation control unit 19 triggers respective ventilation strokes of the ventilation apparatus 11.

The information obtained with respect to patient flow and the trigger signals are transmitted to the analyzer unit 15. There, the patient cardiac cycle phases are compared to the time-dependent occurrence of the triggered ventilating strokes and a characteristic coincidence between the cardiac activity and the ventilation strokes is determined. Stated otherwise, a determination is made as to whether the previously set condition is satisfied or is present or not.

The analyzing unit 15 determines a segment of the patient cardiac cycle during which cycle the trigger sensitivity can be increased to avoid cardiogenic triggering and during which cycle such an increase most likely prevents a satisfaction of the previously fixed or determined condition.

A synchronous reduction of the trigger sensitivity can be adjusted during this determined segment (or segments) or during this phase (or phases) by means of unit 17 based on the available information. This can take place in a stepwise manner.

According to the invention, for the first time, a method is provided for operating an anesthesia or ventilation apparatus for avoiding cardiogenic triggering of a triggered ventilating stroke. The invention further provides an apparatus for carrying out the method of the invention.

It is understood that the foregoing description is that of the preferred embodiments of the invention and that various changes and modifications may be made thereto without departing from the spirit and scope of the invention as defined in the appended claims.

What is claimed is:

1. A method of operating an anesthesia and/or ventilation apparatus including a triggering unit, the method comprising the steps of:
   determining whether a predetermined relationship is present between a patient cardiac cycle and a triggering of a triggered ventilation stroke based on patient flow data and on data of said patient cardiac cycle; and,
   in response to a presence of said predetermined relationship, increasing a triggering threshold for triggered ventilation strokes during only one segment of said patient cardiac cycle so as to cause said predetermined relationship to no longer be present,
   wherein said triggering threshold is increased in a segment of said patient cardiac cycle which begins in a range of 30 to 60 ms after completion of a QRS complex,
   comprising the further steps of: when the start of at least 80% of the triggered respiratory strokes of a viewed time span lies 30 to 60 ms after completion of the QRS complex and/or the cardiac frequency and the respiratory frequency deviate no more than 20% from each other, then determining, utilizing data taken from an electrocardiogram, that said relationship between said patient cardiac cycle and the triggering of a triggered ventilation stroke is present, and
   limiting the time of increasing said triggering threshold until the return of a patient flow to the value of zero.

2. The method of claim 1, comprising the further step of increasing said triggering threshold in such a manner that the start of at most 60% of the triggered respiratory strokes of a viewed time span lies at 30 ms to 60 ms after completion of the QRS-complex and the respiratory frequency and the cardiac frequency deviate by more than 20% from each other.

3. The method of claim 1, comprising the further step of obtaining said data of said patient cardiac flow utilizing an electrocardiogram.

4. The method of claim 1, comprising the further step of stepwise increasing said triggering threshold.

5. The method of claim 4, wherein said triggering threshold is increased in steps of between 0.5 liter/min and 8 liter/min.

6. The method of claim 1, comprising the further step of: during a time span of 30 ms to 60 ms after completion of the QRS-complex until the completion of a T-wave in the electrocardiogram or until the return of the patient flow to a value of zero, increasing said triggering threshold in such a manner that a maximum in the patient flow curve is determined and that several such maxima are averaged over an averaging time span; and, using the averaged maxima as an increase amount for said triggering threshold.

7. The method of claim 6, wherein said averaging time span lies between 50 and 70 seconds.

8. An anesthesia and/or ventilation apparatus comprising:
   a triggering unit for triggering a triggered ventilation stroke when reaching a triggering threshold;
   a determination unit for determining whether a predetermined relationship is present between a patient cardiac cycle and the triggering of triggered ventilation strokes based on patient flow data and on data of said patient cardiac cycle; and, an adjusting unit for increasing said triggering threshold during only one segment of said patient cardiac cycle, when said relationship is present, wherein said determination unit, utilizing data taken from electrocardiograms, is adapted to determine that said relationship is present when the start of at least 80% of the triggered respiratory strokes of a predetermined time span lies 30 to 60 ms after completion of a QRS complex and/or the cardiac frequency and the respiratory frequency deviate no more than 20% from each other, and is adapted to limiting the time of increasing said triggering threshold until the return of a patient flow to the value of zero.

9. The anesthesia and/or ventilation apparatus of claim 8, wherein said adjusting unit is adapted for a stepwise increase of said triggering threshold.

10. The anesthesia and/or ventilating apparatus of claim 8, further comprising a device for recording an electrocardiogram.

11. An apparatus for operating an anesthesia and/or ventilation apparatus comprising:

a triggering unit;

means for determining whether a predetermined relationship is present between a patient cardiac cycle and a triggering of a triggered ventilation stroke based on patient flow data and on data of said patient cardiac cycle;

means for increasing a triggering threshold for triggered ventilation strokes during only one segment of said patient cardiac cycle so as to cause said predetermined relationship to no longer be present in response to a presence of said predetermined relationship, means for determining that said relationship is present when the start of at least 80% of the triggered respiratory strokes of a predetermined time span lies 30 to 60 ms after completion of a QRS complex and/or the cardiac frequency and the respiratory frequency deviate no more than 20% from each other, and means for limiting the time of increasing said triggering threshold until the return of a patient flow to the value of zero.

* * * * *